US011369292B2

(12) United States Patent
Kim

(10) Patent No.: US 11,369,292 B2
(45) Date of Patent: Jun. 28, 2022

(54) PORTABLE APPARATUS FOR NONINVASIVELY MEASURING BLOOD GLUCOSE LEVEL AND OPERATING METHOD THEREOF

(71) Applicant: Hoon Kim, Singapore (SG)

(72) Inventor: Hoon Kim, Singapore (SG)

(73) Assignee: SEEDEVICE INC., Buena Park, CA (US)

( * ) Notice: Subject to any disclaimer, the term of this patent is extended or adjusted under 35 U.S.C. 154(b) by 893 days.

(21) Appl. No.: 15/430,524

(22) Filed: Feb. 12, 2017

(65) Prior Publication Data

US 2018/0228413 A1   Aug. 16, 2018

(51) Int. Cl.
*A61B 5/145* (2006.01)
*A61B 5/1455* (2006.01)
*A61B 5/00* (2006.01)

(52) U.S. Cl.
CPC ........ *A61B 5/14532* (2013.01); *A61B 5/1455* (2013.01); *A61B 5/7278* (2013.01); *A61B 5/681* (2013.01); *A61B 2562/0242* (2013.01)

(58) Field of Classification Search
None
See application file for complete search history.

(56) References Cited

U.S. PATENT DOCUMENTS

| 6,031,603 A * | 2/2000 | Fine | A61B 5/14552 356/41 |
| 2003/0139672 A1* | 7/2003 | Cane | A61B 5/443 600/473 |
| 2005/0075547 A1* | 4/2005 | Wang | A61B 5/0073 600/316 |
| 2005/0154322 A1* | 7/2005 | Eda | A61B 5/14553 600/504 |

(Continued)

FOREIGN PATENT DOCUMENTS

| WO | WO2016/056015 | * | 4/2016 | G01J 3/14 |
| WO | WO2017115361 | * | 6/2017 | A61B 5/145 |

*Primary Examiner* — Jacqueline Cheng
*Assistant Examiner* — Jairo H Portillo
(74) *Attorney, Agent, or Firm* — Renaissance IP Law Group LLP

(57) ABSTRACT

Provided is a method for measuring blood glucose levels of a subject with a portable apparatus for noninvasively measuring blood glucose levels including at least one light receiving element for detecting light by using different light integration times, including: (a) switching on an LED for emitting light having wavelength absorbed in or scattered by glucose; (b) measuring a first signal value according to light which is reflected off the surface skin layer of the subject and enters in response to a first light integration time in the situation where the light is radiated; (c) adjusting a second light integration time for measuring light reflected off the inner skin layer of the subject based on the first signal value; (d) measuring a second signal value according to the light which is reflected off the inner skin layer of the subject and (Continued)

enters in response to the adjusted second light integration time; and (e) producing the blood glucose level of the subject by using a third signal value according to light which enters due to an ambient environment and the second signal value in the situation where the LED is switched off.

13 Claims, 9 Drawing Sheets

(56) References Cited

U.S. PATENT DOCUMENTS

| | | | |
|---|---|---|---|
| 2007/0156030 A1* | 7/2007 | Richardson | A61B 5/0006 600/300 |
| 2009/0156915 A1* | 6/2009 | Cross | A61B 5/0066 600/316 |
| 2009/0202116 A1* | 8/2009 | Winther | A61B 5/14532 382/128 |
| 2010/0016689 A1* | 1/2010 | Kanayama | A61B 5/1491 600/316 |
| 2010/0292549 A1* | 11/2010 | Shuler | A61B 5/0215 600/324 |
| 2012/0010477 A1* | 1/2012 | Amano | A61B 5/0075 600/301 |
| 2013/0049604 A1* | 2/2013 | Pan | H05B 37/0218 315/151 |
| 2013/0056806 A1* | 3/2013 | Kim | H01L 27/14645 257/290 |
| 2014/0275869 A1* | 9/2014 | Kintz | A61B 5/14532 600/310 |
| 2015/0173631 A1* | 6/2015 | Richards | A61B 5/7282 600/479 |
| 2016/0097716 A1* | 4/2016 | Gulati | A61B 5/7267 250/339.01 |
| 2016/0192867 A1* | 7/2016 | Esenaliev | A61B 5/0095 600/316 |
| 2016/0242683 A1* | 8/2016 | Ishiguro | A61B 5/1455 |
| 2016/0246326 A1* | 8/2016 | von Badinski | G01P 15/00 |
| 2017/0209053 A1* | 7/2017 | Pantelopoulos | A61B 5/02125 |

* cited by examiner (a)

(b)

PORTABLE APPARATUS FOR NONINVASIVELY MEASURING BLOOD GLUCOSE LEVEL AND OPERATING METHOD THEREOF

The present disclosure relates to an apparatus for noninvasively measuring blood glucose levels and more particularly to a portable apparatus for noninvasively measuring blood glucose levels, which is conveniently carriable and wearable and is capable of measuring blood glucose levels more accurately by compensating for an error according to the skin characteristics of a subject, and an operating method thereof.

DESCRIPTION OF THE RELATED ART

It is necessary for those who are sensitive to a change in blood glucose levels such as patients with diabetes to monitor the blood glucose level that undergoes sharp changes in their daily life including exercise, meals and others. Therefore, there is a tendency for conventional apparatuses for invasively measuring blood glucose levels to become smaller in terms of size. However, such apparatuses go with hygiene and safety issues in that it is required that blood should be drawn for using them.

Recently, research and development are performed regarding apparatuses for measuring blood glucose levels in a noninvasive mode while such apparatuses using light are gaining special interest.

A typical apparatus for noninvasively measuring blood glucose levels, which uses light, generally makes use manly of near infrared rays having wavelength in range of 1,100 to 1,600 nm, which are absorbed in the covalent bonds of C—H, O—H and others of glucose. Because almost all of the rays which range roughly from 1,100 to 1,600 nm in terms of wavelength are absorbed into other biogenic substances, for example water ($H_2O$), as illustrated in FIG. 1, light the intensity of which is over a certain value is necessary or various techniques are further required such as polarized spectroscopy in order to separate related components from each other. Moreover, light sources such as white halogen tungsten lamps or laser diodes (LDs), which are not easy to miniaturize or lower power consumption, are required for this range of wavelengths while it is not easy, based on existing technology, to use light sources such as light emitting diodes (LEDs), which are easy to miniaturize and lower power consumption.

A typical silicon photodiode (PD) detector (hereinafter referred to also as a "photodetecting unit") detects mainly those rays which range from 400 to 1,100 nm in terms of wavelength, not the rays the wavelength of which ranges from 1,100 to 1,600 nm as introduced above. Among these light sources, those which range from 800 to 900 nm have the largest depth of penetration. This range of wavelengths is called optical window because less light is absorbed into water and interrupted with other substances such as hemoglobin in this range.

When such a silicon PD is employed as a detector for achieving the apparatus for noninvasively measuring blood glucose levels, the apparatus can be miniaturized because it is possible to make use of wavelengths which range from 400 to 1,100 nm. However, because a sufficiently high value of SN (signal to noise) ratio is required so as to measure glucose contained in blood in small quantities (about 0.01%) by employing the silicon PD as a detector, a high-sensitivity photodetector should be used. Meanwhile, because the maximum electrostatic capacity of a PD which detects light is in proportion to the light receiving area, such a PD employed as a detector should have a considerably large light receiving area so as to detect the response signals of the trace of glucose in blood. As a result, it is not easy to realize the portable apparatus for noninvasively measuring blood glucose that falls within the tolerance, i.e. 10 mg/dL, which is inevitably required for such an apparatus to come into common use, by sufficiently enlarging the light receiving area of the silicon PD used for portable or wearable devices.

In this regard, in order to solve the problems of the existing technology and fit into portable devices, technology to miniaturize and lower the power consumption of the apparatus for noninvasively measuring blood glucose by using, as the light source, typical LEDs which emit light having wavelength in range of 400 to 1,000 nm instead of white halogen tungsten lamps or LDs is increasingly demanded.

The above information disclosed in this Background section is only for enhancement of understanding of the background of the disclosure and it may therefore contain information that does not form the prior art that is already known to a person of ordinary skill in the art.

SUMMARY OF THE DISCLOSURE

In order to solve these problems of the existing technology, the present disclosure provides the apparatus for noninvasively measuring blood glucose levels which is capable of accurately measuring the glucose levels in blood even by using LEDs, which are capable of being miniaturized and lowering power consumption, instead of white halogen tungsten lamps or LDs, which are not easily miniaturized and do not easily lower power consumption.

In addition, the present disclosure provides the apparatus for noninvasively measuring blood glucose levels which ensures accurate measuring results independently of the biometric characteristics inherent to a user who wears the apparatus such as skin color and skin tissue among others.

An aspect of the present disclosure provides the operating method for the portable apparatus for noninvasively measuring blood glucose levels, which includes at least one light receiving element for detecting light based on different amounts of light integration time to measure the blood glucose level of a subject. More particularly, the method includes:

(a) switching on an LED for emitting light having wavelength absorbed in or scattered by glucose;

(b) measuring a first signal value according to light which is reflected off the surface skin layer of the subject and enters in response to a first light integration time in the situation where the light is emitted;

(c) adjusting a second light integration time for measuring light reflected off the inner skin layer of the subject based on the first signal value;

(d) measuring a second signal value according to the light which is reflected off the inner skin layer of the subject and enters in response to the adjusted second light integration time; and (e) producing the blood glucose level of the subject by using a third signal value according to light which enters due to an ambient environment and the second signal value in the situation where the LED is switched off.

The step (c) includes: producing a compensating value by correcting the first signal value by subtracting a first reference value established with reference to a standard subject from the first signal value (c-1); and adjusting the second light integration time by matching relative reflectivity of the compensating value with a light integration time adjustment table previously stored (c-2).

The step (e) includes: calculating a glucose concentration measurement of the subject based on the difference between the second signal value and the third signal value (e-1); and producing the blood glucose level of the subject by matching the produced glucose concentration measurement with a blood glucose level table previously stored (e-2).

The step (e-1) includes: providing feedback of the difference between the second signal value and the third signal value to driving current of the LED or to each of the light integration times which are different from each other when the difference is not equal to a second reference value established in connection with the blood glucose level table (e-1-1); and repeating the steps (b) through (e) until the difference and the second reference value become equal to each other (e-1-2).

In addition, the surface skin layer includes the epidermis and part of the dermis while the inner skin layer includes the dermis and part of subcutaneous tissue.

Some aspect of the present disclosure includes:
(a) switching on the LED which emits light absorbed in or scattered by glucose;
(b) measuring the first signal value according to light which is reflected off the surface skin layer of the subject and enters in response to the first light integration time in the situation where the light is emitted from the LED;
(c) repeating the step (b) by providing feedback of the first signal value to the driving current of the LED until the first signal value and the first reference value established with reference to the standard subject become equal to each other;
(d) measuring the second signal value according to light which is reflected off the inner skin layer of the subject and enters in response to the second light integration time in the situation where the light generated by the driving current to which the feedback is provided is radiated; and
(e) producing the blood glucose level of the subject by using the third signal value according to light which enters due to ambient environmental conditions and the second signal value in the situation where the LED is switched off.

Another aspect of the present disclosure includes:
(a) switching on the LED which emits light absorbed in or scattered by glucose;
(b) measuring the first signal value according to light which is reflected off the surface skin layer of the subject and enters in response to the first light integration time in the situation where the light is emitted from the LED;
(c) adjusting a third light integration time based on the first light integration time to measure light reflected off the inner skin layer of the subject after the light is radiated by the LED;
(d) measuring the second signal value according to light which enters due to ambient environmental conditions after switching the LED off;
(e) measuring the third signal value according to light which is reflected off the inner skin layer of the subject and enters in response to the adjusted third light integration time after switching the LED off; and
(f) producing the blood glucose level of the subject by using the second signal value and the third signal value.

Some aspect of the present disclosure provides the portable apparatus for noninvasively measuring blood glucose levels, including:
the LED which emits light absorbed in or scattered by glucose;
the photodetecting unit which includes at least one light receiving element for receiving light by using different amounts of the light integration time and converts the incident light into an electrical signal; and
a control unit which is connected to the LED and the photodetecting unit, switches the LED on, measures the first signal value according to the light which is reflected off the surface skin layer of the subject and enters in response to the first light integration time, adjusts the second light integration time for measuring the light reflected off the inner skin layer of the subject based on the first light integration time, measures the second signal value according to the light which is reflected off the inner skin layer of the subject and enters in response to the adjusted second light integration time by using the photodetecting unit and produces the blood glucose level of the subject by using the third signal value according to light which enters the photodetecting unit due to ambient environmental conditions and the second signal value in the situation where the LED is switched off.

Some aspect of the present disclosure provides the portable apparatus for noninvasively measuring blood glucose levels, including:
the LED which emits light absorbed in or scattered by glucose;
the photodetecting unit which includes at least one light receiving element for receiving light by using different amounts of the light integration time and converts the incident light into an electrical signal; and
the control unit which is connected to the LED and the photodetecting unit, switches the LED on, measures the first signal value according to the light which is reflected off the surface skin layer of the subject and enters in response to the first light integration time, repeatedly measures the first signal value until the first signal value becomes equal to the first reference value established with reference to the standard subject by providing the feedback of the first signal value to the driving current of the LED, measures the second signal value according to the light which is reflected off the inner skin layer of the subject and enters in response to the second light integration time by using the photodetecting unit in the situation where the light generated by the driving current to which the provided feedback is radiated and produces the blood glucose level of the subject by using the third signal value according to the light which enters the photodetecting unit due to ambient environmental conditions and the second signal value in the situation where the LED is switched off.

Some aspect of the present disclosure provides the portable apparatus for noninvasively measuring blood glucose levels, including:
the LED which emits light absorbed in or scattered by glucose;
the photodetecting unit which includes at least one light receiving element for receiving light by using different amounts of the light integration time and converts the incident light into an electrical signal; and
the control unit which is connected to the LED and the photodetecting unit, switches the LED on, measures the first signal value according to the light which is reflected off the surface skin layer of the subject and enters in response to the first light integration time, adjusts the third light integration time for measuring the light reflected off the inner skin layer of the subject based on the first signal value after the LED emits light, measures the second signal value according to the light which enters the photodetecting unit due to ambient environmental conditions by using the photodetecting unit after switching the LED off, measures the third signal value according to the light which is reflected off the inner skin layer of the subject and enters in response to the adjusted third light integration time by using the photodetecting unit after switching the LED on and produces the blood glucose level of the subject by using the second signal value and the third signal value.

According to an embodiment of the present disclosure, it is possible to obtain measurements by driving multiple pieces of the photodetecting unit for different periods of the light integration time and based on the measurements, to measure reliable blood glucose levels independently of the difference in the skin structures and skin colors among the subjects, ambient environmental light and the like. In addition, according to some embodiment of the present disclosure, it is possible to achieve the portable apparatus for measuring blood glucose levels which is capable of measuring sufficiently reliable blood glucose levels and being miniaturized enough to be worn on a human body even when a single one of the typical LEDs is used as the light source.

BRIEF DESCRIPTION OF THE SEVERAL VIEWS OF THE DRAWING

The above and other features and advantages of the present disclosure will be more clearly understood from the following detailed description taken in conjunction with the accompanying drawing, in which.

Figure 1:
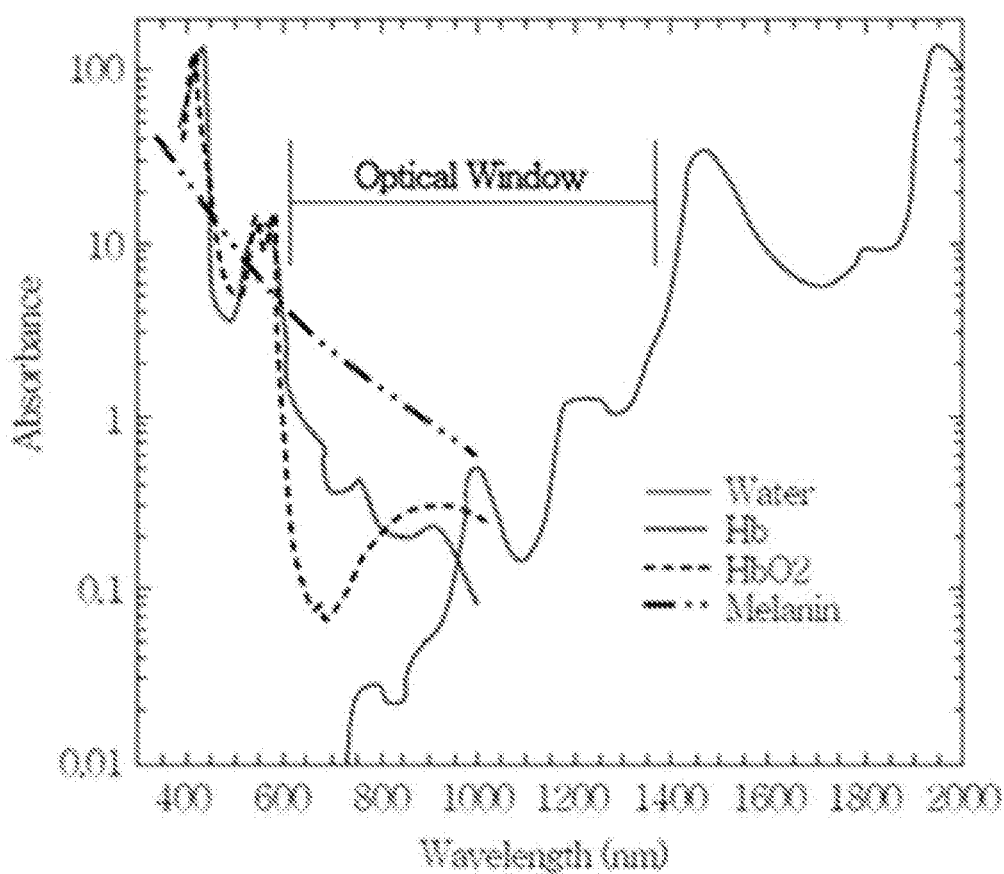
FIG. 1 is a graph, which shows light absorbance in terms of wavelength in biogenic substances.

Although the present disclosure can be embodied in many different forms, only a few specific embodiments are exemplified in the accompanying drawing, which will be described in detail. However, the present disclosure should not be limited to the specific embodiments and should be construed as including all conversions, equivalents and replacements included in the thoughts and technical scope disclosed. When it is determined that detailed description on related known technology for describing the embodiments, such detailed description will be omitted.

Terms such as a first, a second and the like may be used for describing various technical features, which should not be limited to such terms. Such terms are used only for the purpose of distinguishing a feature from another one.

Terms in the present application are used only for describing the specific embodiments and are not used with the intention of limiting the scope of patent rights. A singular form includes its plural form unless the context otherwise requires explicitly different meaning. Terms such as 'include', 'have' and the like in the present application specify that there exists the feature, figure, step, action, component, part or combination of them stipulated in the present specification and should not be construed as excluding in advance the existence or the possible addition of one or more other features, figures, steps, actions, components, parts or combination of them.

The present disclosure will be described more fully hereinafter with reference to the accompanying examples, where same or corresponding features are given an identical reference character and related description that would otherwise be duplicated will be omitted.

Figure 2:
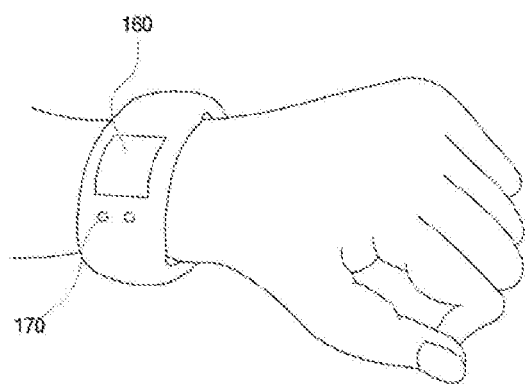
FIG. 2 is a conceptual diagram, which illustrates the components of the portable apparatus for noninvasively measuring blood glucose levels according to an embodiment of the present disclosure.
Figure 2:
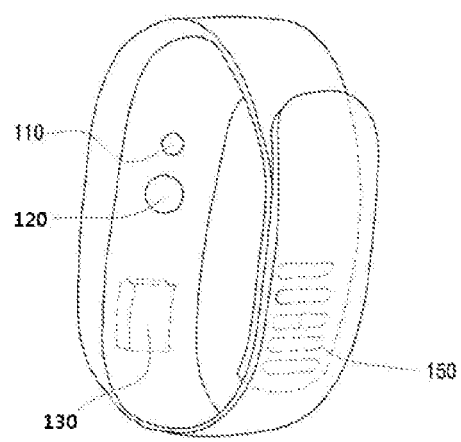

FIG. 2 is a conceptual diagram which illustrates the components of the portable apparatus for noninvasively measuring blood glucose levels according to an embodiment of the present disclosure.

Referring to FIG. 2, the portable apparatus for noninvasively measuring blood glucose levels 100 (hereinafter the "blood glucose level measuring apparatus" for convenience) could be realized in the form of a wearable device, which is worn on a human body part, such as a watch or smart band to be worn on the wrist, a smart ring worn on the finger and the like. Hereinafter, an example realized in the form of a wearable watch will be described.

The blood glucose level measuring apparatus 100 includes the LED 110 and the photodetecting unit 120, which are arranged on its inner surface, which faces the wrist of a wearer and could include, on its outer surface, a display unit 160 and a user interface 170. In addition, the blood glucose level measuring apparatus has the control unit 120 inside the blood glucose level measuring apparatus and could further include a fastening mechanism 150 so that the blood glucose level measuring apparatus is worn on the wrist.

The LED 110 radiates light with wavelength between 800 to 1,000 nm and is absorbed in or scattered by glucose, which is the target to measure with the blood glucose level measuring apparatus 100 according to the present disclosure. Therefore, the light, the LED 110 emits is absorbed in or scattered by glucose particles.

The photodetecting unit 120 detects the intensity of the light which is radiated from the LED 110 and scattered by and then reflected off body tissue. It is desirable to realize the photodetecting unit 120 according to the present disclosure by using the tunnel junction light receiving element, which requires a smaller light receiving area, so that the blood glucose level measuring apparatus according to the present disclosure is easy to miniaturize. The tunnel junction light receiving element could be selected from the high-sensitivity light receiving elements disclosed in U.S. Pat. No. 8,569,806, Unit pixel of image sensor and photo detector thereof, U.S. Pat. No. 8,610,234 and others. The tunnel junction light receiving element has a structure in which a thin dielectric film joined between two conductors or semiconductors and refers to an element which operates based on the tunneling effect that occurs in such a dielectric film.

The tunnel junction light receiving element controls the current in an internal channel of the photodetecting unit 120 because a change in the quantity of electric charges of a light receiving unit acts as the field effect, whereas a typical photodiode distinguishes brightness based only on the quantity of electric charges accumulated in the capacity. In addition, a signal could be amplified within the tunnel junction light receiving element itself. Therefore, the photodetecting unit 120 is capable of generating a photocurrent flow that is several hundred times of that of an existing photodiode with an identical amount of the light integration time by using the tunnel junction light receiving element. Consequently, the photodetecting unit 120 could be miniaturized irrespective of the entire size of the blood glucose level measuring apparatus 100. The photodetecting unit 120 employing the tunnel junction light receiving element will be described in detail below with reference to FIG. 6.

The first LED 110 and the photodetecting unit 120 are arranged on the same surface so that both of them face an identical surface of the subject. The photodetecting unit 120 measures the quantity of the light which is radiated from the LED 110 and scattered by, and then reflected off the glucose particles inside the subject tissue.

The control unit 130 includes at least one component for controlling the LED 110 and the photodetecting unit 120. For example, the control unit 130 includes at least one core and could further include a digital signal processor (DSP), a microprocessing unit (MPU), a microcontroller unit (MCU) and the like.

The control unit 130 measures the scattered, or reflected quantity of the light scattered by and then reflected off the glucose in the subject by controlling the LED 110 and the photodetecting unit 120, quantifies the glucose concentration based on the measured quantity of light and measures the blood glucose level in the body of the subject based on the quantified glucose concentration.

Figure 3:
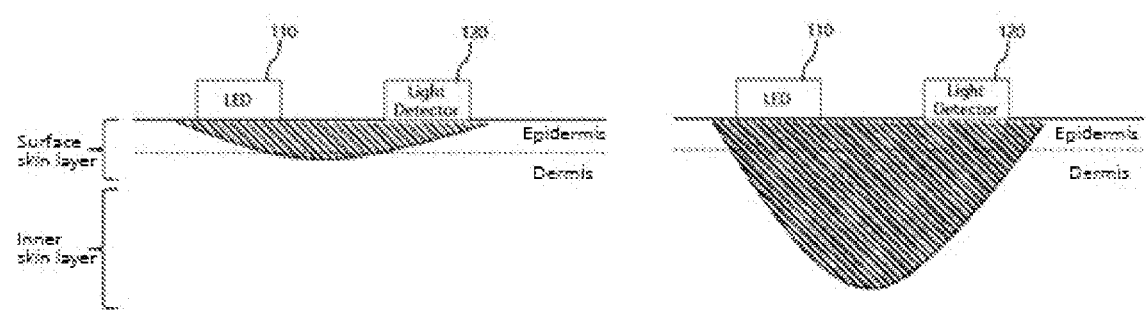
FIG. 3 is a diagram which plots penetration depth of the light, which the LED emits into the subject according to driving modes of the portable apparatus for noninvasively measuring blood glucose levels according to an embodiment of the present disclosure.
Figure 4:
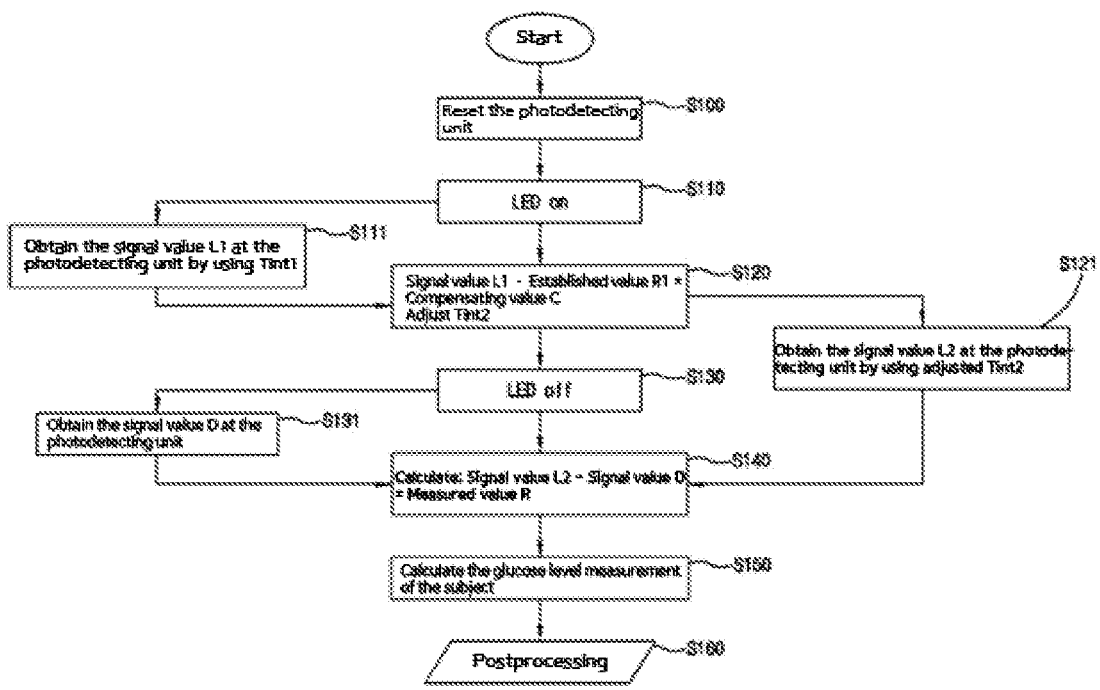
FIG. 4 is a flowchart, which describes a process through which the portable apparatus for noninvasively measuring blood glucose levels according to an embodiment of the present disclosure measures blood glucose levels.

Measurements of the blood glucose level measuring apparatus 100 can vary depending on the biometric characteristics inherent to the wearer such as skin colors, temperature and tissue composition of the subject. Therefore, the control unit 130 measures the light radiated from the LED 110 for different amounts of the light integration time so as to correct the displacement of the measurements due to the characteristics inherent to the wearer. As illustrated in FIG. 3, the light integration time includes: a first light integration time, Tint 1, for measuring the reflected light which enters the photodetecting unit 120 in response to a time, Td1, for which the light the LED 110 emits and penetrates into the surface skin layer, or the epidermis and part of the upper portion of the dermis, as represented as the hatched area in FIG. 3(a), of the subject, where almost no glucose exists, and then is scattered and reflected therefrom; and a second light integration time, Tint 2, for measuring the reflected light by using the photodetecting unit 120 in response to a time, Td2, for which the light the LED 110 emits and penetrates down to the inner skin layer, or the dermis and part of the subcutaneous tissue thereunder, as represented as the hatched area in FIG. 3(b), of the subject, where glucose exists, and then is scattered and reflected therefrom. In this mode, the control unit 130 quantifies the measured glucose concentration independently of the wearer characteristics and is capable of ensuring an identical measuring result for an identical blood glucose level. FIG. 4 describes the process through which the blood glucose level measuring apparatus 100 measures the blood glucose level of the subject while FIG. 5 lists the signals measured in the process of FIG. 4 in a time series mode.

Referring to FIG. 4, as a premeasurement step, the control unit 130 resets the photodetecting unit 120 when the LED 110 is switched off.

Figure 5:
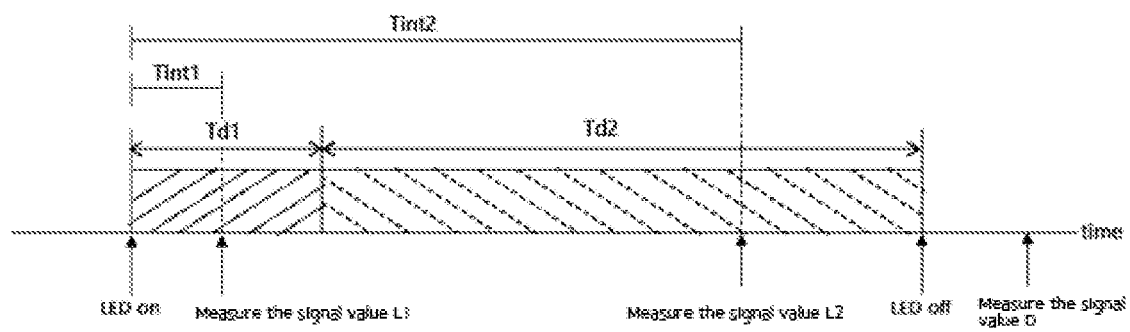
FIG. 5 is a diagram, which lists signals measured in the process of FIG. 4 in a time series mode.

After that, in the situation where LED 110 is switched on in order to radiate light onto the subject S110, the control unit 130 measures a signal value, L1 due to the light, which is reflected off the surface skin layer of the subject and then enters during the first light integration time, Tint1, by using the photodetecting unit 120 S111. As illustrated in FIG. 5, Tint1 corresponds to a period from the moment the light begins to be radiated to a point before Td1 and can be considerably short (e.g. about 0.01 μs). Therefore, the signal value L1 contains reflectivity of the surface skin layer and contains only the effect of the skin characteristics and the like of the subject.

After that, the control unit 130 calculates the compensating value C by using the measured signal value L1 and the first reference value or established value R1 S210. The compensating value C is an offset produced by correcting the signal value L1 by subtracting the established value R1 from the signal value L1 and the control unit 130 adjusts Tint2 of the photodetecting unit 120 by using the compensating value C. For example, the control unit 130 is capable of adjusting Tint2 by matching the relative reflectivity of the compensating value C with the light integration time adjustment table previously stored, wherein the adjusted value of Tint2 cannot exceed the value of Td2. Meanwhile, the established value R1 can be a value established by experimentally measuring the light reflected off the surface skin layer with reference to the standard subject.

After that, the control unit 130 measures a signal value, L2, generated by the light which is reflected off the inner skin layer of the subject and enters in response to the adjusted value of Tint2 by using the photodetecting unit 120 in the situation where light is radiated onto the subject S121, wherein the adjusted value of Tint2 is a period from the moment the light begins to be radiated to a point before Td2, as illustrated in FIG. 5, and can be, for example, about 1 ms or longer. Therefore, the glucose concentration is incorporated into the signal value L2.

After that, the control unit 130 switches the LED 110 off S130. In addition, the control unit 130 resets the photodetecting unit 120.

After that, the control unit 130 measures a signal value, D, according to the light which enters the photodetecting unit 120 due to an ambient environment in the situation where the LED 110 is switched off S131. The signal value D is a value wherein effects of ambient environmental light and temperature are incorporated without the glucose because the signal value D was measured when the LED 110, the light source of the wavelengths which are absorbed in glucose, is not driven. In some cases, the signal value D can be measured after resetting the photodetecting unit S100 and before switching the LED 110 on, or before S110 in order to measure the signal value L1.

After that, the control unit 130 produces the glucose concentration measurement, measured value R, by using the obtained signal values D and L2 S140. The measured value R is an offset produced by correcting the signal value L2 by subtracting the signal value D from the signal value L2 and the control unit 130 matches the measured value R with the blood glucose level table established to be corresponding to each glucose concentration to produce the corresponding blood glucose level S150. The blood glucose level table can be stored in the blood glucose level measuring apparatus and each value, which constitutes the blood glucose level table could be a value produced based on the results obtained by using an invasive blood glucose level measuring apparatus simultaneous with the noninvasive blood glucose level measuring apparatus according to the present disclosure.

Meanwhile, in S140, when the measured value R is not equal to the second reference value, or established value R2, established in connection with the blood glucose level table, the control unit 130 is capable of providing feedback of the measured value R to the intensity of lighting, or the amount of the driving current, of the LED 110 or to the light integration time, Tint1 and Tint2, of the photodetecting unit 120. The blood glucose level measuring apparatus 100 is capable of adjusting the quantity of light for measuring in this way in order to correct the quantity of light so that a constant quantity of light is radiated onto the subject independently of external factors such as ambient environmental light, temperature and the like, save for the skin characteristics of the subject.

Although it has been described that the control unit 130 adjusts Tint2 by using the compensating value C in S120, the control unit is capable of adjusting the driving current, or intensity of lighting, of the LED 110 by using the compensating value C depending on embodiments to achieve, which will be described later with reference to FIG. 7.

Through this process, the blood glucose measuring apparatus 100 is capable of correcting the errors caused by the skin color, skin characteristics, body temperature and others inherent to the subject and the quantity of light by incorporating the errors generated by the ambient external factors, thereby practically correcting the blood glucose level without being influenced by the internal and external factors and obtaining constant measurements.

Meanwhile, the high-sensitivity detector should be used for the photodetecting unit in order to detect a minute change in the glucose inside the subject. The tunnel junction light receiving element is used in the present disclosure as an example of the high-sensitivity detector.

Figure 6:
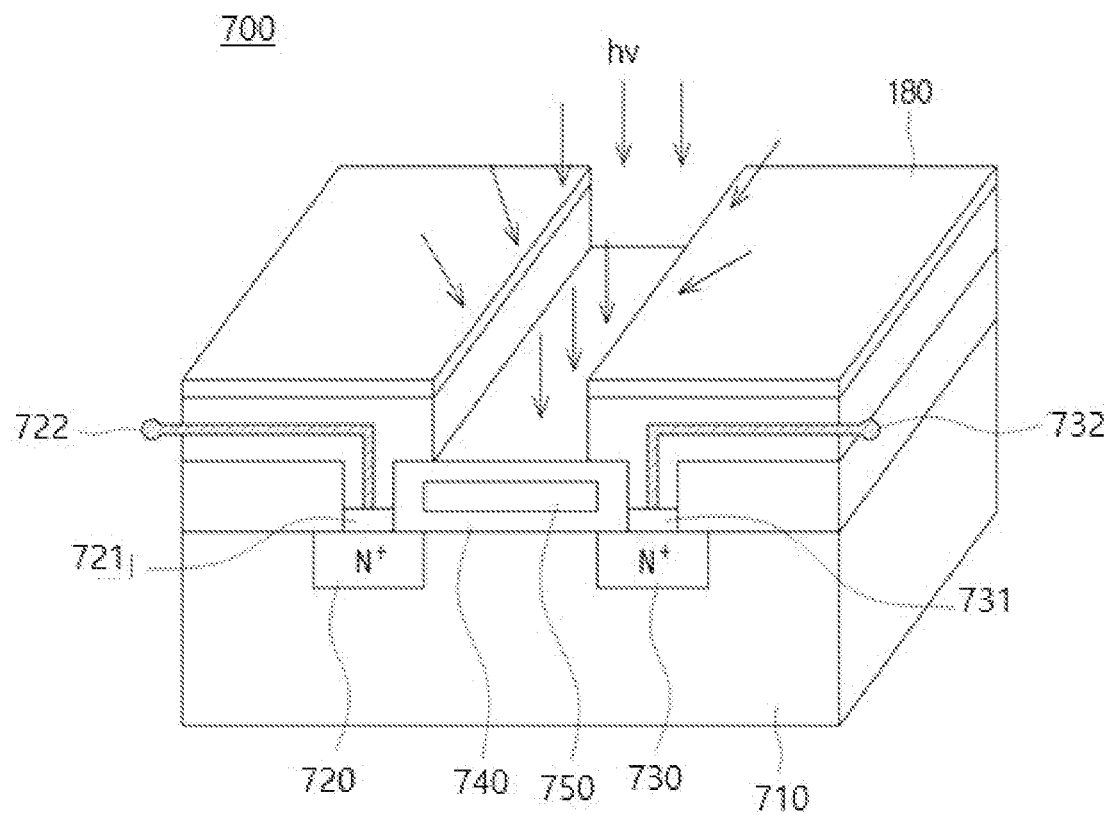
FIG. 6 is a diagram, which illustrates an exemplary structure of a tunnel junction light receiving element used as the detector for the portable apparatus for noninvasively measuring blood glucose levels according to an embodiment of the present disclosure.

FIG. 6 illustrates an example of the tunnel junction light receiving element to achieve the photodetecting unit 120 according to an embodiment of the present disclosure. The tunnel junction light receiving element has a structure in which the thin dielectric film joined between two conductors or semiconductors and refers to an element which operates based on the tunneling effect that occurs in such a dielectric film.

The tunnel junction light receiving element 700 could have an, e.g., n-MOSFET structure, wherein the tunnel junction light receiving element 700 is formed on a P-type substrate 710 and includes an N+ diffusion layer 720 and another N+ diffusion layer 730, which corresponds the source and the drain, respectively, of a typical NMOS electronic element. The N+ diffusion layers 720, 730 will be referred to as the "source" and the "drain", respectively, of the tunnel junction light receiving element 700 hereinafter.

Metallic contacts 721, 731 are formed on the source 720 and the drain 730 and each of the metallic contacts 721, 731 is connected to the exterior via each of metallic lines 722, 732.

The thin dielectric film 740 is formed between the source 720 and the drain 730 while polysilicon 750 which corresponds to the gate of a typical NMOS structure is formed above the dielectric film 740, wherein P-type impurities are doped in the polysilicon 750. The polysilicon 750 acts as the light receiving unit for receiving light in the tunnel junction light receiving element 700. The polysilicon 750 will be referred to as the "light receiving unit".

The light receiving unit 750 are separated from the source 720 and the drain 730 with the dielectric film 740. The tunneling effect occurs between the light receiving unit 750 and the source 720 or the drain 730, wherein it is desirable for the dielectric film 740 to have a thickness of 10 nm or less for promoting the tunneling effect.

When light having its energy higher than the binding energy of the impurities doped above the light receiving unit 750 and the band gap of the polysilicon is radiated, electron-hole pairs are generated due to light excitation in the light receiving unit 750 and the electrons and the holes, which constitute the generated electron-hole pairs, exist in the state of electrons and holes, respectively, for a specific period until they are recombined. The separated electrons move freely outside the grain boundary of the light receiving unit 750. Here, when voltage is applied to the source 720 or the drain 730, the electrons are accumulated near the boundary of the light receiving unit 750 adjacent to the source or the drain, which generates a specific amount of electric field between the source 720 and the drain 730 and the light receiving unit 750.

As the strength of the generated electric field increases, the tunneling occurs more easily near the boundary between the source 720 and the drain 730 and the light receiving unit 750. At the instant certain energy level conditions are met near the boundary, the tunneling of the accumulated electrons occurs. By this phenomenon, the electrons accumulated near the boundary of the light receiving unit 750 tunnel the dielectric film 740 to transfer to the source 720 or the drain 730. This is equivalent to an increase of the number of holes, or the quantity of positive charges, as many as the number of the electron lost, which lowers the channel threshold voltage, thereby causing a current flow via the channel.

The light receiving element with this structure is capable of generating a photocurrent flow that is more than several hundred up to thousand times of that of an existing photodiode at an identical quantity of light. A typical photodiode distinguishes brightness based only on the quantity of electric charges accumulated in the capacity. On the contrary, the tunnel junction light receiving element 700 generates a large current flow in the channel because a minute change in the quantity of electric charges of a light receiving unit 750 due to light acts as a large amount of the field effect. In addition, electric charge is supplied infinitely via the drain when necessary, which provides an effect of amplifying the signal within the light receiving element itself. Therefore, because an independent signal amplifying element is not required and because this technology could be achieved in a small area, it is possible to realize the blood glucose level measuring apparatus according to the present disclosure in the form of the small wearable device such as wearable watches and rings by forming the photodetecting unit by using the tunnel junction light receiving element.

Figure 7:
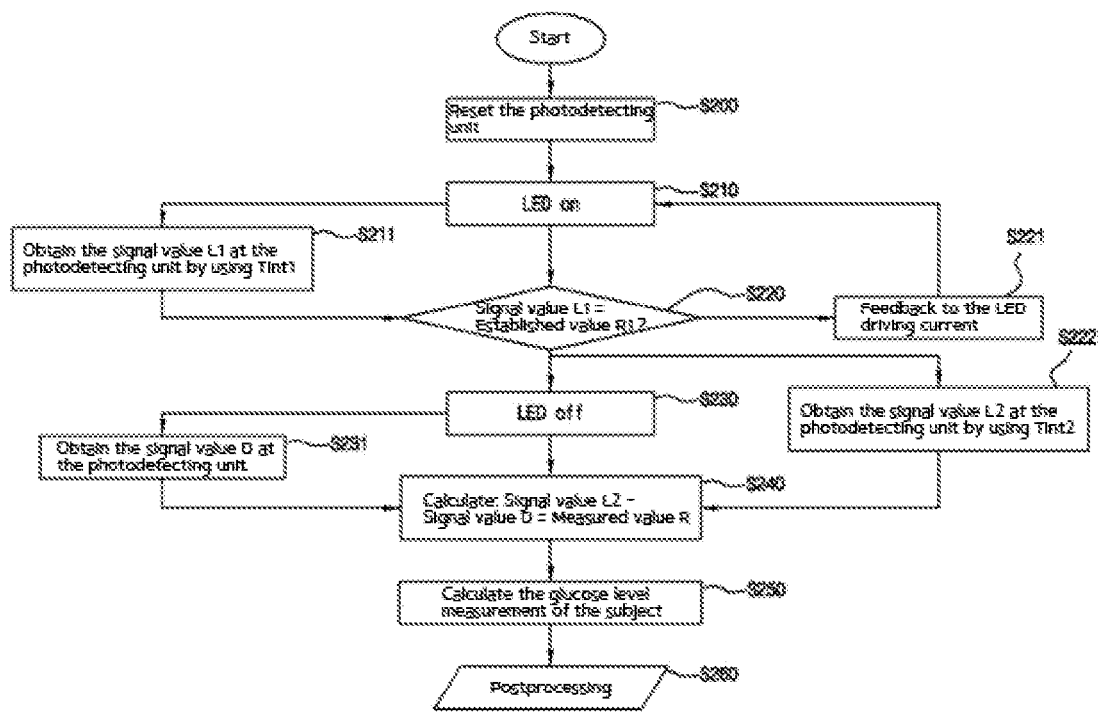
FIG. 7 is another flowchart, which describes the process through which the portable apparatus for noninvasively measuring blood glucose levels according to an embodiment of the present disclosure measures blood glucose levels.

FIG. 7 describes another process through which the blood glucose measuring apparatus 100 measures the blood glucose level of the subject.

Referring to FIG. 7, the control unit 130 resets the photodetecting unit 120 in the situation the LED 110 is switched off.

After that, the control unit 130 measures the signal value L1 S211 generated by the light which is reflected off the surface skin layer of the subject and enters in response to Tint1 by using the photodetecting unit 120 in the situation where the control unit switched on the LED in order to emit light onto the subject S210.

After that, when the measured signal value L1 is not equal to the first reference value, or the established value R1 of FIG. 4, established with reference to the standard subject S220, the control unit 130 provides feedback of the signal value L1 to the driving current of the LED 110 S221. More specifically, the control unit 130 is capable of reducing the radiated quantity of light by reducing the driving current of the LED 110 when the result from subtracting the measured value R1 from the signal value L1 is positive. On the contrary, the control unit 130 is capable of increasing the radiated quantity of light by increasing the driving current of the LED 110 when the result from subtracting the measured value R1 from the signal value L1 is negative. In this way, the control unit 130 is capable of correcting the light so that a constant quantity of light is radiated onto the subject at all times independently of the skin characteristics of the subject. Meanwhile, the steps S211 through S221 can be repeated multiple times until the measured signal value L1 and the established value R1 become equal to each other within a tolerance or before Td1 passes.

After that, the control unit 130 measures the signal value L2 S222 generated by the light which is reflected off the inner skin layer of the subject and then enters in response to Tint2 by using the photodetecting unit S120 in the situation where the light generated by the driving current to which the feedback has been provided is radiated onto the subject.

After that, the control unit 130 switches the LED 110 on S230. In addition, the control unit 130 resets the photodetecting unit 120.

After that, the control unit 130 measures the signal value D generated by the light which enters the photodetecting unit 120 due to the ambient environment S231 in the situation where the LED 110 is switched off. After that, the control unit 130 produces the glucose concentration measurement, or the measured value R, by using the obtained signal value D and the obtained signal value L2 S240. In addition, the control unit 130 matches the measured value R with the blood glucose level table established to be corresponding to each glucose concentration to produce the corresponding blood glucose level S250.

Meanwhile, the control unit 130 is capable of providing feedback of the measured value R to the driving current of the LED 110 or the light integration time, Tint1 and/or Tint2, of the photodetecting unit 120 when the measured value R is not equal to the second reference value, or the established value R2, established in connection with the blood glucose level table. The blood glucose level measuring apparatus 100 is capable of adjusting the quantity of light for measuring in this way in order to correct the quantity of light so that a constant quantity of light is radiated onto the subject independently of the external factors such as ambient environmental light, temperature and the like, save for the skin characteristics of the subject.

Figure 8:
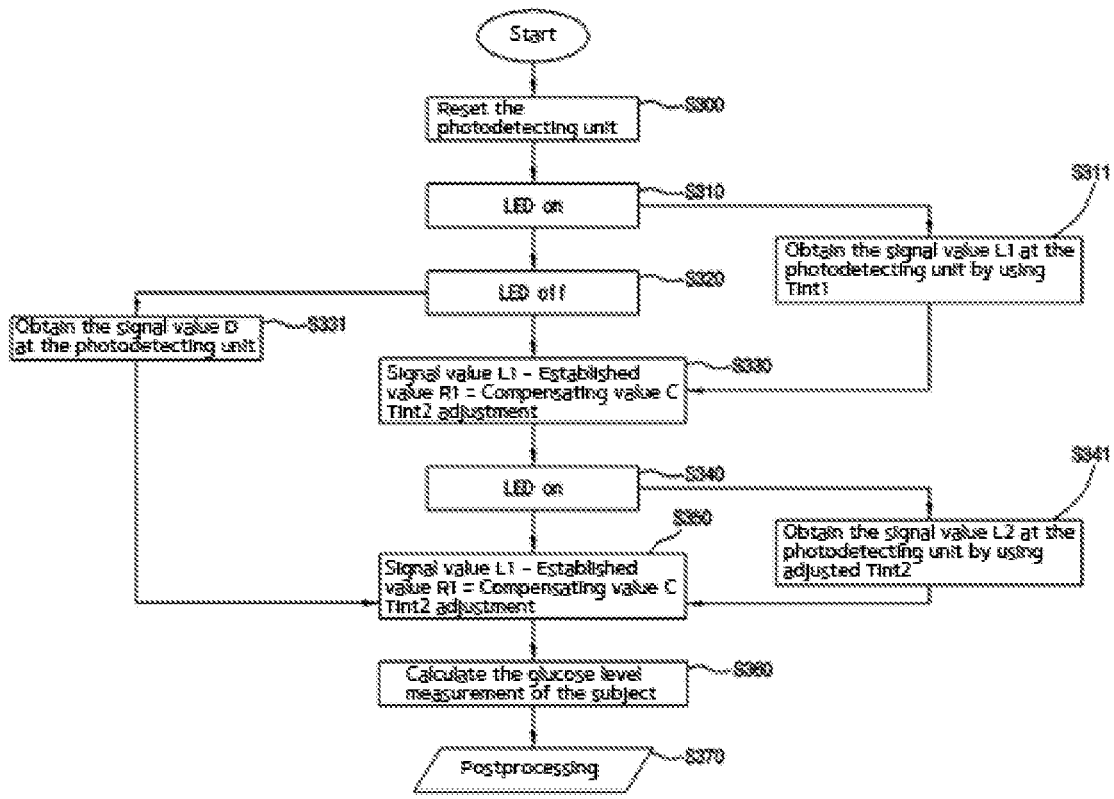
FIG. 8 is still another flowchart, which describes the process through which the portable apparatus for noninvasively measuring blood glucose levels according to an embodiment of the present disclosure measures blood glucose levels.
Figure 9:
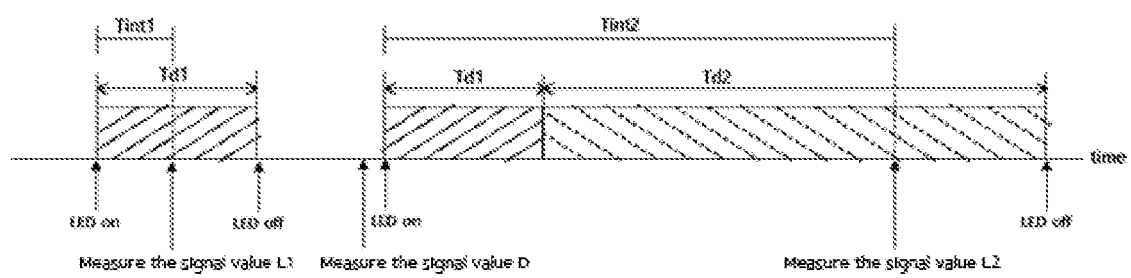
FIG. 9 is a diagram, which lists signals measured in the process of FIG. 8 in a time series mode.

FIG. 8 describes yet another process through which the blood glucose level measuring apparatus 100 measures the blood glucose level of the subject while FIG. 9 is a diagram which lists signals measured in the process of FIG. 8 in a time series mode.

Referring to FIGS. 8 and 9, as the premeasurement step, the control unit 130 resets the photodetecting unit 120 when the LED 110 is switched off.

After that, in the situation where LED 110 is switched on in order to radiate light onto the subject S310, the control unit 130 measures the signal value, L1, due to the light which is reflected off the surface skin layer of the subject and then enters in response to the first light integration time, Tint1, by using the photodetecting unit 120 S311. As illustrated in FIG. 9, the first light integration time, Tint1, should be shorter than Td1, for which the light penetrates into the surface skin layer, or the epidermis and part of the upper portion of the dermis, where almost no glucose exists, and then is scattered and reflected therefrom and can be, for example, about 0.01 μs.

After that, when Td1 passes, the control unit 130 switches the LED 110 off S320 in order to reduce the error which can be generated in the following step of measuring the signal value L2 with the various factors which occur during the step of measuring the signal value L1, by resetting the photodetecting unit.

The control unit 130 produces the compensating value C by using the measured signal value L1 and the first reference value, or the established value R1 of FIG. 4, and adjusts the second light integration time, Tint2, of the photodetecting unit 120 by using the compensating value C. As illustrated in FIG. 9, Tint2 is the time for which the light emitted when the LED 110 is switched on penetrates into the inner skin layer, or the dermis and part of the subcutaneous tissue thereunder, and is scattered and reflected therefrom and should be longer than Td1 and shorter than the sum of Td1 and Td2. The control unit 130 is capable of adjusting Tint2 by matching the relative reflectivity of the compensating value C with the light integration time adjustment table previously stored.

After that, the control unit 130 switches the LED 110 on S340. The control unit 130 measures the signal value L2 according to the light which is reflected off the inner skin layer of the subject and enters in response to the adjusted light integration time Tint2 by using the photodetecting u nit 120 S341.

After that, the control unit 130 produces the glucose concentration measurement, or the measured value R2, by using the obtained signal values D and L2 S350. The measured value R2 is an offset produced by correcting the signal value L2 by subtracting the signal value D from the signal value L2 and the control unit 130 matches the measured value R2 with the blood glucose level table established to be corresponding to each glucose concentration to produce the corresponding blood glucose level S360.

Meanwhile, the control unit 130 is capable of providing feedback of the measured value R2 to the driving current of the LED 110 or the light integration time, Tint1 and/or Tint2, of the photodetecting unit 120 when the measured value R2 is not equal to the second reference value, or the established value R2, established in connection with the blood glucose level table. The blood glucose level measuring apparatus 100 is capable of adjusting the quantity of light for measuring in this way in order to correct the quantity of light so that a constant quantity of light is radiated onto the subject independently of the external factors such as ambient environmental light, temperature and the like, save for the skin characteristics of the subject.

In the appended Claims, an element described as a means to perform a specific function includes any arbitrary methods to perform the specific function and such an element is capable of including the combination of circuit elements to perform the specific function or software in an arbitrary form which is combined with a suitable circuit to perform software to perform the specific function and includes firmware, microcode and the like.

Referring to the expression of "an embodiment" specified in the present specification and its various derivatives signifies that specific features, structures, characteristics and the like with regard to the embodiment are included in at least one among the embodiments of the principle of the present disclosure. Therefore, the expression of "an embodiment" and arbitrarily selected other modified examples disclosed across the whole of the present disclosure do not refer to an identical embodiment at all times.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended Claims.

REFERENCE CHARACTERS

100: Portable apparatus for noninvasively measuring blood glucose level
110: First LED
120: Photodetecting unit
130: Control unit

What is claimed is:

1. A method for measuring blood glucose levels of a subject with a wearable device worn on a wrist for noninvasively measuring blood glucose levels comprising one light receiving unit corresponding to at least one tunnel junction light receiving element for detecting light by using different light integration times, the method comprising the following steps:

(a) switching on an LED for emitting light having wavelength absorbed in or scattered by glucose, wherein the LED and the light receiving unit are arranged on an inner surface of the wearable device, and the light receiving unit is separated from a source and a drain by a dielectric film formed between the source and the drain;

(b) measuring a first signal value according to light which is reflected off a surface skin layer of the subject and enters to the light receiving unit during a first light integration time when the light is radiated and a tunneling effect occurs between the light receiving unit and the source or the drain, wherein the first light integration time is set within a first time duration and the at least one tunnel junction light receiving element is reset after measuring the first signal value, wherein step (b) comprises:

(b-1) providing a feedback of the first signal value to a driving current of the LED; and (b-2) repeatedly measuring the first signal value by reducing or increasing radiated quantity of light, using the driving current, based on a result of subtracting a first reference value established with reference to a standard subject from the first signal value, until the result is less than a tolerance or before the first time duration passes; and (c) adjusting a second light integration time for measuring light reflected off an inner skin layer of the subject based on a final first signal value at the end of the repeated measurement in step (b-2), wherein the second light integration time is adjusted within a second time duration, after the first time duration passed, wherein step (c) comprises:

(c-1) producing a compensating value by correcting the final first signal value by subtracting the first reference value from the final first signal value; and (c-2) adjusting the second light integration time by matching relative reflectivity of the compensating value with a light integration time adjustment table previously stored;

(d) measuring a second signal value according to the light which is reflected off the inner skin layer of the subject and enters to the light receiving unit during the adjusted second light integration time, wherein the at least one tunnel junction light receiving element is reset after measuring the second signal value and switching the LED off when the second time duration is passed; and (e) producing the blood glucose level of the subject by using a third signal value measured after the second time duration according to light which enters due to an ambient environment when the LED is switched off and the second signal value.

2. The method for measuring blood glucose levels of claim 1, wherein step (e) comprises:

(e-1) producing a glucose concentration measurement of the subject based on the difference between the second signal value and the third signal value; and (e-2) producing the blood glucose level of the subject by matching the produced glucose concentration measurement with a blood glucose level table previously stored.

3. The method for measuring blood glucose levels of claim 2, wherein step (e-1) comprises:

(e-1-1) providing feedback of the difference between the second signal value and the third signal value to driving current of the LED or the first light integration time or the second light integration time when the difference is not equal to a second reference value established in connection with the blood glucose level table; and (e-1-2) repeating steps (b) through (e) until the difference and the second reference value become equal to each other.

4. The method for measuring blood glucose levels of claim 1, wherein the surface skin layer comprises the epidermis and part of the dermis while the inner skin layer comprises the dermis and part of subcutaneous tissue.

5. A non-transitory computer readable recording medium, on which a program is recorded to achieve the method of claim 1.

6. A method for measuring blood glucose levels of a subject with a wearable device worn on a wrist for noninvasively measuring blood glucose levels comprising one light receiving unit corresponding to at least one tunnel junction light receiving element for detecting light by using different light integration times, comprising the following steps:

(a) switching on an LED for emitting light having wavelength absorbed in or scattered by glucose, wherein the LED and the light receiving unit are arranged on an inner surface of the wearable device, and the light receiving unit is separated from a source and a drain by a dielectric film formed between the source and the drain;

(b) measuring a first signal value according to light which is reflected off a surface skin layer of the subject and enters to the light receiving unit during a first light integration time when the light is radiated and a tunneling effect occurs between the light receiving unit and the source or the drain, wherein the first light integration time is set within a first time duration and the at least one tunnel junction light receiving element is reset after measuring the first signal value;

(c) repeating step (b) by reducing or increasing radiated quantity of light based on a result of subtracting a first reference value established with reference to a standard subject from the first signal value and by providing feedback of the first signal value to a driving current of the LED until the result of the subtraction is less than a tolerance or before the first time duration passes;

(d) measuring a second signal value according to the light which is reflected off an inner skin layer of the subject and enters to the light receiving unit during a second light integration time when light generated by a final driving current at the end of the repeated measurement in step (c) to which the feedback is provided is radiated, wherein the second light integration time is adjusted within a second time duration after the first time duration passed, wherein the at least one tunnel junction light receiving element is reset after measuring the second signal value and switching the LED off when the second time duration is passed, wherein step (d) comprises:

(d-1) producing a compensating value by correcting a final first signal value at the end of the repeated measurement in step (c) by subtracting the first reference value from the final first signal value; and (d-2) adjusting the second light integration time by matching relative reflectivity of the compensating value with a light integration time adjustment table previously stored; and (e) producing the blood glucose level of the subject by using a third signal value measured after the second time duration according to light which enters due to the ambient environment when the LED is switched off and the second signal value.

7. The method for measuring blood glucose levels of claim 6, wherein step (b) is repeatedly performed by reducing the driving current of the LED when the result from subtracting the first reference value from the first signal value is positive and step (b) is repeatedly performed by increasing the driving current of the LED when the result from subtracting the first reference value from the first signal value is negative in step (c).

8. A method for measuring blood glucose levels of a subject with a wearable device worn on a wrist for noninvasively measuring blood glucose levels comprising one light receiving unit corresponding to at least one tunnel junction light receiving element for detecting light by using different light integration times, comprising the following steps:

(a) switching on an LED for emitting light having wavelength absorbed in or scattered by glucose, wherein the LED and the light receiving unit are arranged on an inner surface of the wearable device, and the light receiving unit is separated from a source and a drain by a dielectric film formed between the source and the drain;

(b) measuring a first signal value according to light which is reflected off a surface skin layer of the subject and enters to the light receiving unit during a first light integration time when the light is radiated and a tunneling effect occurs between the light receiving unit and the source or the drain, wherein the first light integration time is set within a first time duration and the at least one tunnel junction light receiving element is reset after measuring the first signal value, wherein step (b) comprises:

(b-1) providing a feedback of the first signal value to a driving current of the LED; and (b-2) repeatedly measuring the first signal value by reducing or increasing radiated quantity of light, using the driving current, based on a result of subtracting a first reference value established with reference to a standard subject from the first signal value, until the result is less than a tolerance or before the first time duration passes; and (c) adjusting a third light integration time for measuring light reflected off an inner skin layer of the subject based on a final first signal value at the end of the repeated measurement in step (b-2) after the light is radiated by the LED, wherein the third light integration time is adjusted within a second time duration after the first time duration passed, wherein step (c) comprises:

(c-1) producing a compensating value by correcting the final first signal value by subtracting the first reference value from the final first signal value; and (c-2) adjusting the third light integration time by matching relative reflectivity of the compensating value with a light integration time adjustment table previously stored;

(d) switching the LED off when the first time duration is passed and measuring a second signal value according to the light which enters due to the ambient environment after switching the LED off, wherein the at least one tunnel junction light receiving element is reset after measuring the second signal value;

(e) measuring a third signal value according to the light which is reflected off the inner skin layer of the subject and enters to the light receiving unit during the adjusted third light integration time after switching the LED on; and (f) producing the blood glucose level of the subject by using the second signal value and the third signal value.

9. A wearable device worn on a wrist for noninvasively measuring blood glucose levels, the wearable device comprising:

an LED to emit light absorbed in or scattered by glucose;

a photodetecting unit which comprises at least one tunnel junction light receiving element for receiving light by using different amount of a light integration time and converts an incident light into an electrical signal, wherein the photodetecting unit corresponds to one light receiving unit; and a control unit connected to the LED and the photodetecting unit, the control unit configured to:

switch the LED on, wherein the LED and the light receiving unit are arranged on an inner surface of the wearable device, and the light receiving unit is separated from a source and a drain by a dielectric film formed between the source and the drain, measure a first signal value according to light which is reflected off a surface skin layer of a subject and enters to the light receiving unit during a first light integration time when the light is radiated and a tunneling effect occurs between the light receiving unit and the source or the drain, wherein the first light integration time is set within a first time duration and the at least one tunnel junction light receiving element is reset after measuring the first signal value, repeat to measure the first signal by reducing or increasing radiated quantity of light based on a result of subtracting a first reference value established with reference to a standard subject from the first signal value and by providing feedback of the first signal value to driving current of the LED until the result of the subtraction is less than a tolerance or before the first time duration passes, produce a compensating value by correcting a final first signal value at the end of the repeated measurement by subtracting the first reference value from the final first signal value, adjust a second light integration time for measuring the light reflected off an inner skin layer of the subject based on the final first signal value and the first light integration time, wherein the second light integration time is adjusted within a second time duration, after the first time duration has passed, wherein the second light integration time is adjusted based on the final first signal and by matching relative reflectivity of the compensating value with a light integration time adjustment table previously stored, measure a second signal value according to the light which is reflected off the inner skin layer of the subject and enters to the light receiving unit during the second light integration time by using the photodetecting unit, wherein the at least one tunnel junction light receiving element is reset after measuring the second signal value, switches the LED off when the second time duration is passed; and produce a blood glucose level of the subject by using a third signal value measured after the second time duration according to light which enters the photodetecting unit due to the ambient environment when the LED is switched off and the second signal value.

10. The wearable device worn on a wrist for noninvasively measuring blood glucose levels of claim 9, wherein the control unit produces a compensating value by correcting the first signal value by subtracting a first reference value established with reference to a standard subject from the first signal value and adjusts the second light integration time by matching a relative reflectivity of the compensating value with a light integration time adjustment table previously stored.

11. The wearable device worn on a wrist for noninvasively measuring blood glucose levels of claim 9, wherein the control unit produces a glucose concentration measurement of the subject based on a difference between the second signal value and the third signal value and produces the blood glucose level of the subject by matching the produced glucose concentration measurement with a blood glucose level table previously stored.

12. The wearable device worn on a wrist for noninvasively measuring blood glucose levels of claim 11, wherein the control unit provides feedback of the difference between the second signal value and the third signal value to a driving current of the LED or the first light integration time or the second light integration time when the difference is not equal to a second reference value established in connection with the blood glucose level table.

13. A wearable device for noninvasively measuring blood glucose levels, the wearable device comprising:
an LED which emits light absorbed in or scattered by glucose;

a photodetecting unit which includes at least one tunnel junction light receiving element for receiving light by using different amounts of a light integration time and converts incident light into an electrical signal, wherein the photodetecting unit corresponds to one light receiving unit; and a control unit connected to the LED and the photodetecting unit, the control unit configured to:

switch the LED on, wherein the LED and the light receiving unit are arranged on an inner surface of the wearable device, and the light receiving unit is separated from a source and a drain by a dielectric film formed between the source and the drain, measure a first signal value according to light which is reflected off a surface skin layer of a subject and enters to the light receiving unit during a first light integration time when the light is radiated and a tunneling effect occurs between the light receiving unit and the source or the drain and the at least one tunnel junction light receiving element is reset after measuring the first signal value, repeat to measure the first signal by reducing or increasing radiated quantity of light based on a result of subtracting a first reference value established with reference to a standard subject from the first signal value and by providing feedback of the first signal value to driving current of the LED until the result of the subtraction is less than a tolerance or before a first time duration passes, produce a compensating value by correcting a final first signal value at the end of the repeated measurement by subtracting the first reference value from the final first signal value, adjust a third light integration time for measuring light reflected off an inner skin layer of the subject based on the final first signal value after the LED emits light and the first time duration has passed, wherein the third light integration time is adjusted based on the final first signal and by matching relative reflectivity of the compensating value with a light integration time adjustment table previously stored, measure a second signal value according to light which enters the photodetecting unit due to the ambient environment by using the photodetecting unit after switching the LED off, wherein the at least one tunnel junction light receiving element is reset after measuring the second signal value, measure a third signal value according to light which is reflected off the inner skin layer of the subject and enters to the light receiving unit during the third light integration time by using the photodetecting unit after switching the LED on and produces a blood glucose level of the subject by using the second signal value and the third signal value.

* * * * *